（12） United States Patent
Maltz

(10) Patent No.: US 11,951,332 B2
(45) Date of Patent: Apr. 9, 2024

(54) SYSTEMS AND METHODS FOR SCINTILLATION CAMERA-BASED MOTION TRACKING IN RADIOTHERAPY

(71) Applicant: SHANGHAI UNITED IMAGING HEALTHCARE CO., LTD., Shanghai (CN)

(72) Inventor: Jonathan Maltz, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 17/818,979

(22) Filed: Aug. 11, 2022

(65) Prior Publication Data

US 2022/0379141 A1 Dec. 1, 2022

Related U.S. Application Data

(63) Continuation of application No. 16/857,203, filed on Apr. 24, 2020, now Pat. No. 11,446,522.

(51) Int. Cl.
*A61N 5/10* (2006.01)
*G06T 7/00* (2017.01)
(Continued)

(52) U.S. Cl.
CPC ......... *A61N 5/1067* (2013.01); *A61N 5/1049* (2013.01); *A61N 5/1068* (2013.01); *G06T 7/0016* (2013.01); *G06T 7/215* (2017.01); *G06T 11/005* (2013.01); *A61N 2005/1051* (2013.01); *A61N 2005/1052* (2013.01); *A61N 2005/1059* (2013.01)

(58) Field of Classification Search
None
See application file for complete search history.

(56) References Cited

U.S. PATENT DOCUMENTS

| 2003/0112922 A1 | 6/2003 | Burdette et al. |
| 2011/0200171 A1 | 8/2011 | Beetel et al. |
| (Continued) | | |

OTHER PUBLICATIONS

S. Derenzo et al. Cryogenic Scintillation Properties of n-Type GaAs for the Direct Detection of MeV/c2 Dark Matter, Journal of Applied Physics, 2018, 14 pages.
(Continued)

*Primary Examiner* — Hoon K Song
(74) *Attorney, Agent, or Firm* — METIS IP LLC

(57) ABSTRACT

The disclosure provides a system for EGRT. The system may include a radiotherapy device for treating a subject. The radiotherapy device may include a scintillation camera that is directed at an ROI of the subject. The subject may be injected with a radioactive tracer or implanted with a radioactive marker before treatment. The ROI may undergo a physiological motion during the treatment. The system may deliver a treatment session to the subject by the radiotherapy device. During the treatment session, the system may acquire a target image of the ROI indicative of a distribution of the radioactive tracer or the radioactive maker in the ROI by the scintillation camera, and adapt a radiation beam to be delivered to the subject with respect to the physiological motion of the ROI by adjusting the radiation beam based on the target image.

20 Claims, 7 Drawing Sheets

(51) Int. Cl.
*G06T 7/215* (2017.01)
*G06T 11/00* (2006.01)

(56) References Cited

U.S. PATENT DOCUMENTS

| | | |
|---|---|---|
| 2017/0157427 A1 | 6/2017 | Xing et al. |
| 2017/0239494 A1 | 8/2017 | Mazin et al. |
| 2017/0252577 A1* | 9/2017 | Dempsey ............. A61N 5/1031 |
| 2018/0308264 A1 | 10/2018 | Gu et al. |
| 2018/0369611 A1 | 12/2018 | Owens et al. |
| 2019/0070437 A1* | 3/2019 | Olcott ................. A61N 5/1075 |
| 2019/0099619 A1 | 4/2019 | Maltz |
| 2019/0209867 A1 | 7/2019 | Sun et al. |
| 2020/0016432 A1 | 1/2020 | Maolinbay |
| 2021/0154496 A1 | 5/2021 | Maurer et al. |
| 2021/0196212 A1* | 7/2021 | Mazin ................. A61N 5/1081 |

OTHER PUBLICATIONS

First Office Action in Chinese Application No. 202110443169.4 dated Jun. 6, 2022, 10 pages.

\* cited by examiner

500

| Acquiring, by a scintillation camera, a target image of an ROI of the subject indicative of a tracer distribution of a radioactive tracer in the ROI | 501 |

↓

| Adapting a radiation beam to be delivered to the subject with respect to a physiological motion of the ROI by adjusting, based on the target image, the radiation beam | 502 |

601 — Obtaining a plurality of reference images of an ROI corresponding to a plurality of motion phases of the ROI 602 — Obtaining a PET or SPECT image sequence relating to the ROI, each image in the image sequence representing one motion phase of the plurality of motion phases and corresponding to a reference image of the same motion phase 603 — Selecting, among the plurality of reference images, a reference image that matches a target image 604 — Determining, based on the image corresponding to the selected reference image in the image sequence, a target position of the ROI 605 — Adjusting, based on the target position of the ROI, the radiation beam

FIG. 6

SYSTEMS AND METHODS FOR SCINTILLATION CAMERA-BASED MOTION TRACKING IN RADIOTHERAPY

CROSS-REFERENCE TO RELATED APPLICATIONS

This application is a continuation of U.S. patent application Ser. No. 16/857,203, filed on Apr. 24, 2020, the contents of which are hereby incorporated by reference.

TECHNICAL FIELD

The present disclosure generally relates to radiotherapy, and more particularly, systems and methods for scintillation camera-based motion tracking in radiotherapy.

BACKGROUND

Radiation therapy has been widely employed in cancer treatment in which a radiation beam is delivered toward a target (e.g., a tumor) of a subject (e.g., a patient). In radiation therapy, a motion tracking technique may be used to improve the precision of the radiation delivery to the target in the presence of a physiological motion that the target and/or an organ-at-risk (OAR) near the target undergoes. Recently, a positron emission tomography (PET) technique has been used in radiation therapy for tracking the target and/or the ORA in real time. For example, the subject may be injected with a radioactive tracer before treatment, and placed in a radiotherapy device which includes one or more PET detectors during the treatment. PET lines-of-response (LORs) may be monitored during the treatment by the PET detector(s), and the target and/or the OAR may be tracked based on a plurality of 511 keV photon pairs generated within the target and/or the OAR. Typically, an initial PET-computed tomography (CT) scan may be performed before the treatment in order to image the uptake of the injected radioactive tracer. Based on this prior information and the PET measurements during treatment, the position(s) of the target and/or the OAR may be estimated. However, the PET imaging during the treatment may be affected by scattering events and random coincidence events. In addition, the photons and electrons produced in the treatment may interact with scintillation crystals of the PET detector(s), which may result in an afterglow of the scintillation crystals and affect the imaging quality. Therefore, it is desirable to provide methods and systems for motion tracking in radiotherapy, thereby improving the precision of treatment delivery.

SUMMARY

In one aspect of the present disclosure, a system for emission guided radiation therapy (EGRT) is provided. The system may include a radiotherapy device for treating a subject. The radiotherapy device may include a scintillation camera that is directed at a region of interest (ROI) of the subject. The subject may be injected with a radioactive tracer or implanted with a radioactive marker before treatment. The ROI may undergo a physiological motion during the treatment. The system may further include at least one storage device including a set of instructions, and at least one processor configured to communicate with the at least one storage device. When executing the set of instructions, the at least one processor may be configured to direct the system to deliver a treatment session to the subject by the radiotherapy device. During the treatment session, the at least one processor may be configured to direct the system to acquire a target image of the ROI indicative of a distribution of the radioactive tracer or the radioactive maker in the ROI by the scintillation camera, and adapt a radiation beam to be delivered to the subject with respect to the physiological motion of the ROI by adjusting the radiation beam based on the target image.

In some embodiments, to adapt the radiation beam based on the target image, the at least one processor may be configured to direct the system to obtain a plurality of reference images of the ROI corresponding to a plurality of motion phases of the ROI. Each of the reference images may be indicative of a distribution of the radioactive tracer or the radioactive maker in the ROI at a corresponding motion phase. The at least one processor may also be configured to direct the system to determine a target position of the ROI during the acquisition of the target image based on a comparison of the target image and each of the reference images, and adjust the radiation beam based on the target position of the ROI.

In some embodiments, the ROI may include at least one of a target or an OAR near the target. To adjust the radiation beam based on the target position of the ROI, the at least one processor may be configured to direct the system to direct the radiotherapy device to gate a delivery of the radiation beam or aim the radiation beam at the target according to the target position of the ROI.

In some embodiments, to determine a target position of the ROI, the at least one processor may be configured to direct the system to obtain an image sequence relating to the ROI. Each image in the image sequence may represent one motion phase of the plurality of motion phases and correspond to a reference image of the same motion phase. The at least one processor may also be configured to direct the system to select a reference image that matches the target image among the plurality of reference images, and determine the target position of the ROI based on the image corresponding to the selected reference image in the image sequence.

In some embodiments, to obtain a plurality of reference images of the ROI, the at least one processor may be configured to direct the system to generate the plurality of reference images of the ROI according to a simulation algorithm based on the image sequence. The at least one processor may also be configured to direct the system to obtain the plurality of reference images during a scan of the subject by the scintillation camera. The image sequence may be reconstructed based on image data acquired in the scan.

In some embodiments, the scan of the subject may be at least one of a PET scan, a single-photon emission computed tomography (SPECT), or a computed tomography (CT) scan.

In some embodiments, the scintillation camera may be placed close to the body surface of the subject in the treatment session.

In some embodiments, the at least one processor may be configured to direct the system to determine a position of the scintillation camera based on a trajectory of the radiation beam. The scintillation camera may be placed at the determined position during the treatment session.

In some embodiments, the scintillation camera may include at least one of a $LaBr_3$:Ce scintillation camera, a $LaBr_3$(Ce+Sr) scintillation camera, or a cryogenic scintillation camera.

In some embodiments, the scintillation camera may include one or more low-afterglow scintillation crystals, and a collimator operably coupled to the one or more low-afterglow scintillation crystals.

In some embodiments, the radiotherapy device may be a particle radiotherapy device that delivers a particle beam to the subject during the treatment session. The at least one processor may be configured to direct the system to determine a position of a Bragg peak of the particle beam based on the target image, and evaluate the delivery of the treatment session based on the position of the Bragg peak.

In another aspect of the present disclosure, a method for EGRT implemented on a radiotherapy system is provided. The radiotherapy system may include a radiotherapy device for treating a subject. The radiotherapy device may include a scintillation camera that is directed at an ROI of the subject. The subject may be injected with a radioactive tracer or implanted with a radioactive marker before treatment. The ROI may undergo a physiological motion during the treatment. The method may include delivering a treatment session to the subject by the radiotherapy device. During the treatment session, the method may also include acquiring a target image of the ROI indicative of a distribution of the radioactive tracer or the radioactive maker in the ROI by the scintillation camera, and adapting a radiation beam to be delivered to the subject with respect to the physiological motion of the ROI by adjusting the radiation beam based on the target image.

In still another aspect of the present disclosure, a non-transitory computer-readable storage medium is provided. The non-transitory computer-readable storage medium may include a set of instructions for EGRT using a radiotherapy system. The radiotherapy system may include a radiotherapy device for treating a subject. The radiotherapy device may include a scintillation camera that is directed at an ROI of the subject. The subject may be injected with a radioactive tracer or implanted with a radioactive marker before treatment. The ROI may undergo a physiological motion during the treatment. When the set of instructions is executed by at least one processor, the set of instructions may direct the at least one processor to effectuate a method. The method may include delivering a treatment session to the subject by the radiotherapy device. During the treatment session, the method may also include acquiring a target image of the ROI indicative of a distribution of the radioactive tracer or the radioactive maker in the ROI by the scintillation camera, and adapting a radiation beam to be delivered to the subject with respect to the physiological motion of the ROI by adjusting the radiation beam based on the target image.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 5 is a flowchart illustrating an exemplary process for adapting a radiation beam to be delivered to a subject with respect to a physiological motion of a region of interest (ROI) of the subject according to some embodiments of the present disclosure; and FIG. 6 is a flowchart illustrating an exemplary process for adapting a radiation beam to be delivered to a subject based on a target image of the subject according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
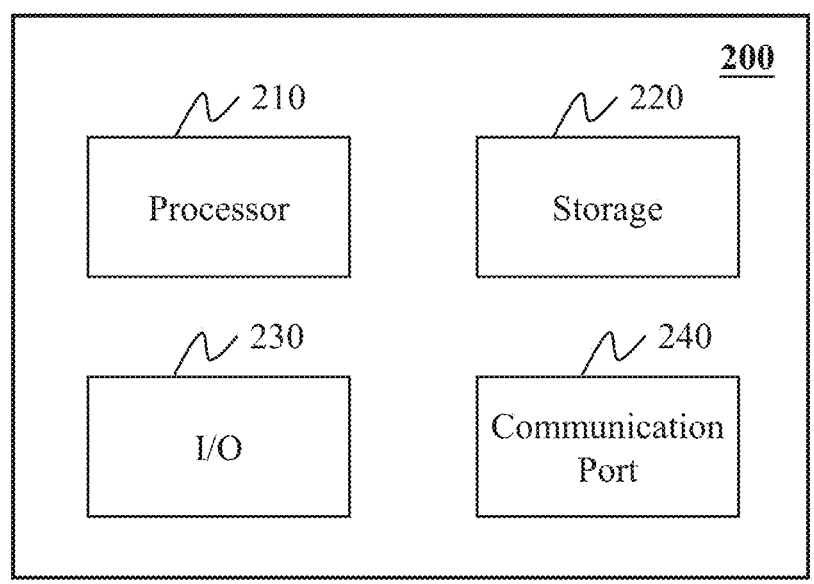
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging and/or treatment, such as for disease diagnosis, treatment or research purposes. In some embodiments, the systems may include a radiotherapy system, a computed tomography (CT) system, an emission computed tomography (ECT) system, an X-ray photography system, a positron emission tomography (PET) system, or the like, or any combination thereof. For illustration purposes, the disclosure describes systems and methods for radiotherapy.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "anatomical structure" in the present disclosure may refer to gas (e.g., air), liquid (e.g., water), solid (e.g., stone), cell, tissue, organ of a subject, or any combination thereof, which may be displayed in an image (e.g., a planning image, or a treatment image, etc.) and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body.

An aspect of the present disclosure relates to systems and methods for emission guided radiation therapy (EGRT). A radiotherapy device may be used to deliver a treatment session to a subject. The radiotherapy device may include a scintillation camera that is directed at a region of interest (ROI) of the subject. The ROI may include a target and/or one or more OARs near the target of the subject that undergo a physiological motion during the treatment session. In order to track the physiological motion of the ROI during the treatment session, the subject may be injected with a radioactive tracer or implanted with a radioactive maker before the treatment session. During the treatment session, the systems and methods may acquire a target image of the ROI, which may be captured by the scintillation camera and indicative of a distribution of the radioactive tracer or the radioactive maker in the ROI. The systems and methods may further adapt a radiation beam to be delivered to the subject with respect to the physiological motion of the ROI by adjusting the radiation beam based on the target image. For example, based on the target image, the systems and methods may determine a target position of the ROI during the acquisition of the target image, and direct the radiotherapy device to gate a delivery of the radiation beam or aim the radiation beam at the target according to the target position of the ROI. In this way, the precision of the radiation beam delivery to the target during the treatment session may be improved.

According to some embodiments of the present disclosure, the scintillation camera may include one or more low-afterglow scintillation crystals and/or one or more high-energy-resolution scintillators, which may improve the imaging quality of the scintillation camera. In addition, the scintillation camera may be placed close to the body surface of the subject (e.g., at a position close to the ROI of the subject) to capture the target image, wherein the proximity of the scintillation camera to the subject may increase the imaging quality of the target image. Also, the scintillation camera may be easily mounted on a radiotherapy device. Moreover, compared with a conventional wide-solid-angle PET detector, the scintillation camera may be less likely to be influenced by random coincidence events and/or scattering events. Using the scintillation camera may allow a more accurate position estimation of the ROI, which in turn, may improve the precision of radiation delivery of the treatment session.

In some embodiments, the target position of the ROI may be determined based on a plurality reference images and a plurality of images (e.g., PET images, SPECT images, or CT images) relating to the subject. Each of the reference images may correspond to a motion phase of the ROI and indicative of a distribution of the radioactive tracer or the radioactive maker in the ROI at a corresponding motion phase. Each of the PET images may correspond to one of the motion phases, and a corresponding relationship may be previously established between the PET image and one of the reference images of the same motion phase. For example, the target image may be compared with the reference images to select a reference image that matches the target image from the reference images. The target position of the ROI may then be determined based on the PET image that corresponds to the selected reference image. Because that the target image captured by the scintillation camera may provide less information (e.g., information for determining the target position of the ROI) than a PET image, the target position of the ROI may be estimated more accurately. Even in cases that the ROI is not clear enough in the target image, an accurate position estimation of the ROI may be achieved based on the corresponding relationship between the PET images and the reference images.

Figure 1A:
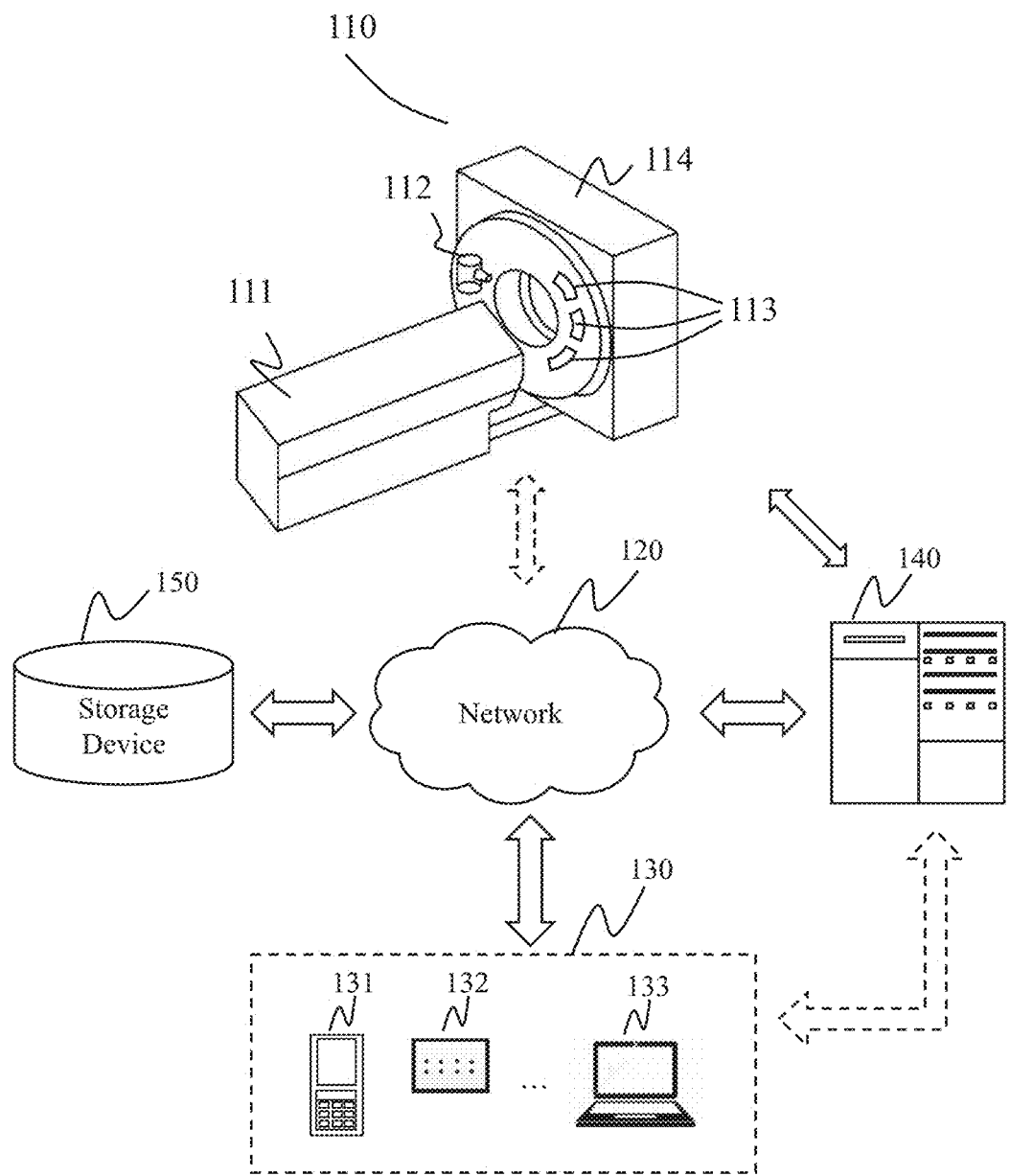
FIG. 1A is a schematic diagram illustrating an exemplary radiotherapy system according to some embodiments of the present disclosure.

FIG. 1A is a schematic diagram illustrating an exemplary radiotherapy system 100 according to some embodiments of the present disclosure. As shown in FIG. 1A, the radiotherapy system 100 may include a radiotherapy device 110, a network 120, one or more terminals 130, a processing device 140, and a storage device 150. In some embodiments, the radiotherapy device 110, the terminal(s) 130, the processing device 140, and/or the storage device 150 may be connected to and/or communicate with each other via a wireless connection (e.g., the network 120), a wired connection, or a combination thereof. The connection between the components of the radiotherapy system 100 may be variable. Merely by way of example, the radiotherapy device 110 may be connected to the processing device 140 through the network 120, as illustrated in FIG. 1A. As another example, the terminal(s) may be connected to the processing device 140 directly or through the network 120. As a further example, the storage device 150 may be connected to the processing device 140 through the network 120 or directly.

The radiotherapy device 110 may be used to delivery a radiotherapy treatment for cancers and other conditions. For example, the radiotherapy device 110 may deliver one or more radiation beams to a treatment region (e.g., a tumor) of a subject for causing an alleviation of the subject's symptom. A radiation beam may include a plurality of radiation beamlets. The subject to be treated may include a body, substance, or the like, or any combination thereof. For example, the subject may include a patient or a part thereof including, e.g., a head, a breast, a lung, a pleura, a mediastinum, an abdomen, a long intestine, a small intestine, a bladder, a gallbladder, a triple warmer, a pelvic cavity, a backbone, extremities, a skeleton, a blood vessel, or the like, or any combination thereof. In some embodiments, the radiotherapy device 110 may be a conformal radiation therapy device, an image-guided radiation therapy (IGRT) device, an intensity-modulated radiation therapy (IMRT) device, an intensity-modulated arc therapy (IMAT) device, an emission guided radiation therapy (EGRT), or the like. In some embodiments, the radiotherapy device 110 may be a radiotherapy device with a C-arm linear accelerator (also referred to as "Linac"), a Tomotherapy device, a Halcyon radiotherapy device, a Cyberknife radiotherapy device, or the like.

In some embodiments, the radiotherapy treatment may be performed on the subject according to a treatment plan. For example, before the radiotherapy treatment on the subject, a planning image (e.g., a CT image) relating to the subject may be acquired via scanning the subject. One or more regions of interest (ROIs) of the subject may be identified based on the image. An ROI disclosed herein may include a region of the subject including at least part of malignant tissue (e.g., a tumor, a cancer-ridden organ, or a non-cancerous target of radiation therapy) and/or other tissue (e.g., a tissue surrounding the malignant tissue). For example, the ROI may include a target and/or one or more an organs-at-risk (OAR) near the target. A target may refer to a certain anatomical structure that needs to be tracked and/or monitored during the radiotherapy treatment. For example, the target may be a tumor, an organ with a tumor, a tissue with a tumor, or any combination thereof, that needs to be treated by radiations. An OAR may include an organ (or a portion thereof) and/or a tissue that are close to the target and not indented to be subjected to radiation but under the risk of radiation damage due to its proximity to the target. The treatment plan may be made based on the identified ROIs. For example, the radiotherapy treatment may include a plurality of treatment sessions (fractions) and last for a treatment period of multiple days (e.g., 2 to 5 weeks). The treatment plan may describe how the radiotherapy treatment is planned to be performed on the subject, more specifically, how one or more beams are delivered to the ROIs during each treatment session over the course of treatment lasting a certain period of time, e.g., days.

As illustrated in FIG. 1A, in some embodiments, the radiotherapy device 110 may include a table 111, a treatment radiation source 112, one or more scintillation cameras 113, and a gantry 114. The table 111 may be configured to support the subject during radiation treatment. The gantry 114 may be configured to support one or more components of the radiotherapy device 110, such as the treatment radiation source 112 and/or the scintillation camera(s) 113. The treatment radiation source 112 may be configured to generate and emit a radiation beam (e.g., an X-ray beam) toward the subject. For example, the radiation beam may include electrons, photons, or other types of radiation. In some embodiments, the treatment radiation source 112 may include a linear accelerator (also referred to as "Linac"). In some embodiments, the radiation beam generated by the treatment radiation source 112 may pass through one or more collimators forming certain shapes, and enter into the subject. In some embodiments, the gantry 114 may rotate, for example, clockwise or counter-clockwise around a gantry rotation axis. The treatment radiation source 112 may rotate along with the gantry 114.

In some embodiments, during a treatment session of the subject, an ROI of the subject may undergo a physiological motion. Taking a patient as an exemplary subject, exemplary ROIs of the patient that undergo a physiological motion may include the heart that undergoes a cardiac motion, a lung that undergoes a respiratory motion, a region (e.g., the brain) filled with blood which forms a blood flow, the stomach that undergoes a gastrointestinal motion, muscle that undergoes a skeletal muscle motion, a chest that has a physiological motion caused by the cardiac motion and the respiratory motion, an abdomen that has a physiological motion caused by the gastrointestinal and the respiratory motion, or the like, or any combination thereof. The physiological motion of the ROI may need to be tracked to ensure that the radiation beam delivered to the subject matches the planned dose distribution as closely as possible.

To this end, a radioactive tracer may be injected into or a radioactive maker may be implanted into the subject before the treatment session starts in order to track the physiological motion of an ROI of the subject. For example, a PET tracer (e.g., fludeoxyglucose (FDG), prostate specific membrane antigen (PSMA)) or a single-photon emission computed tomography (SPECT) tracer (e.g., hexamethyl propylene amine oxime (HMPAO)) may be injected into the subject before the treatment session starts. One or more atoms of the radioactive tracer may be chemically incorporated into biologically active molecules in the subject. The active molecules may become concentrated in a tissue of interest within the subject. For example, the FDG may be taken up significantly in the brain, the bladder, the liver, a kidney, a heart muscle, an active skeletal muscle, and/or one or more tumors. The radioactive tracer may undergo positron emission decay and emit positrons. A positron may travel a certain distance (e.g., about 1 mm) within a tissue of interest, lose kinetic energy, and interact with an electron of the subject. The positron and the electron may annihilate and produce a pair of annihilation photons (or radiation rays). The pair of annihilation photons may move in approximately opposite directions. The annihilation photons (or a portion thereof) may be detected and used to track the physiological motion of the ROI of the subject by performing exemplary processes for physiological motion tracking disclosed herein.

In some embodiments, a radiotracer may also consist of a radionuclide bonded or otherwise associated with a structure such as a nanoparticle, a radio-activated nanoparticle, or a radioactive/radiolabeled drug injected for therapeutic purpose.

Merely by way of example, during the treatment session, the annihilation photons (or a portion thereof) may be detected by the scintillation camera(s) 113. The scintillation camera(s) 113 may generate an image relating to the subject indicative of a distribution of the radioactive tracer or the radioactive maker in the subject. In some embodiments, the scintillation camera(s) 113 may be directed at the ROI of the subject, in order to capture an image relating to the ROI indicative of a tracer distribution in the ROI during the treatment session. For example, if the ROI is the heart of the subject, a scintillation camera 113 may be placed close to the chest of the subject to capture an image indicative of a tracer distribution in the heart, wherein the position of the heart may be determined based on the image captured by the scintillation camera 113. By placing the scintillation camera 113 close to the ROI of the subject, the proximity of the scintillation camera 113 to the ROI may be increased and an image captured by the scintillation camera 113 may have an improved quality, which in turn, may improve the accuracy of the position of the ROI determined based on the captured image.

Optionally, the scintillation camera 113 may be directed to capture images of the subject or a portion thereof including, e.g., an ROI, during the treatment session continuously or intermittently (e.g., periodically) so that the position distribution of the ROI (e.g., the heart) may be tracked in real-time or intermittently. In some embodiments, a scintillation camera 113 may move to different positions, e.g., with the rotation of the gantry 114, to capture image(s) from different perspectives during the treatment session. Alternatively, the scintillation camera 113 may be placed at a fixed position to capture image(s) from a fixed perspective in the treatment session.

In some embodiments, a scintillation camera 113 may be detachably mounted on the radiotherapy device 110 (e.g., the gantry 114, the table 111). For example, as shown in FIG. 1A, the radiotherapy device 110 may include a plurality of scintillation cameras 113 which are arranged in a ring design around the detection tunnel formed by the gantry 114. During a treatment session, all of the scintillation cameras 113 may be actuated to capture images of the subject from their respective perspectives. Alternatively, a portion of the scintillation cameras 113, such as one or more scintillation cameras 113 close to an ROI of the subject, may be actuated to capture image(s) relating to the ROI.

In some embodiments, a scintillation camera 113 may be mounted on the gantry 114 via a retractable and/or movable mechanism. The position of the scintillation camera 113 may be adjusted by adjusting the retractable and/or movable mechanism. For example, the scintillation camera 113 may be placed at a desired position by the retractable and/or movable mechanism during a treatment planning process to avoid that beams traverse the scintillation camera before entry into the subject. In some embodiments, a scintillation camera 113 may share the same gantry 114 as the treatment radiation source 112 as shown in FIG. 1A. Alternatively, the scintillation camera 113 and the treatment radiation source 112 may be mounted on different gantries.

In some embodiments, a scintillation camera 113 may include one or more scintillation crystals (or referred to one or more scintillators). A scintillation crystal may interact with (e.g., excited by) a particle (e.g., an annihilation photon, an electron). In some embodiments, the interaction with the particle may result in an afterglow in the scintillation crystal. For example, the scintillation crystal may have a persistent luminescence after the excitation of the particle. The afterglow may affect the imaging quality of the scintillation crystal. The shorter the afterglow lasts, the faster the scintillation crystal may return to a "dark" state and absorb a new annihilation photon. Thus, in some embodiments, it is desirable to unitize one or more low-afterglow scintillation crystals to improve the imaging quality of the scintillation camera 113. For example, an afterglow of a scintillation crystal may be measured by the fraction of scintillation light still present for a certain time after the particle excitation occurs. A low-afterglow scintillation crystal described herein may refer to a scintillation crystal that has a fraction of scintillation light still present for a certain time after the particle excitation occurs lower than a threshold fraction. Exemplary low-afterglow scintillation crystals may include a $LaBr_3$:Ce scintillator, a $LaBr_3$(Ce+Sr) scintillator, a cryogenic scintillator, a $Gd_2SiO_5$(Ce) scintillator, a $Bi_4Ge_3O_{12}$ scintillator, a $PbWO_4$ scintillator, a $CdWO_4$ scintillator, a TI scintillator, or the like. In some embodiments, one or more high energy resolution scintillators (e.g., a scintillator having an energy resolution higher than a threshold), such as a $LaBr_3$:Ce scintillator and/or a $LaBr_3$(Ce+Sr) scintillator may be unitized in a scintillation camera 113. Such high energy resolution scintillators may improve the imaging quality of the scintillation camera 113.

Optionally, the scintillation camera 113 may include a collimator operably coupled to the scintillation crystal(s) of the scintillation camera 113. The collimator may be used to narrow a path of incoming radiation to the scintillation camera 113. Exemplary collimators may include a parallel-hole collimator, a pinhole collimator, a coded-aperture collimator, or the like. In some embodiments, the scintillation camera 113 may include a coded-aperture collimator and/or a multiple pinhole collimator such that the scintillation camera 113 may localize a gamma-ray source (e.g., an annihilation event, or a single photon event) during imaging.

In some embodiments, compared with using a PET detector to track the physiological motion of an ROI during the treatment session, using the scintillation camera(s) 113 may reduce the influence of random coincidence events and/or scattering events. For example, a scintillation camera 113 may have a relatively smaller solid angle of than a PET detector, thereby being less likely to receive a photon caused by a scattering coincidence event. In addition, because a scintillation camera 113 may have a smaller size, it is easier and more practical to cool the temperature of the scintillation camera 113 to a desired temperature, which may improve the system performance by allowing the use of low-afterglow and high-energy-resolution scintillators.

In some embodiments, the radiotherapy device 110 may include one or more PET detectors and/or one or more SPECT detectors. For illustration purposes, a radiotherapy device 110 including one or more PET detectors are described as an example. The PET detector(s) may be used to acquire PET data relating to the subject before, during, and/or after a treatment session. For example, PET data relating to the subject may be acquired by the PET detector(s) before the treatment session and indicate motion data of an ROI, e.g., positions of the ROI at different motion phases of the ROI. The PET data in combination with one or more images captured by the scintillation camera(s) 113 during the treatment session may be used to track the physiological motion of the ROI as described elsewhere in this disclosure (e.g., FIG. 6 and the relevant descriptions).

In some embodiments, the PET detector(s) may be mounted on the gantry 114 or another gantry of the radiotherapy device 110. For example, the PET detector(s) may be mounted on the gantry 114 out of a treatment plane (i.e., a plane where an isocenter of the treatment radiation source 112 locates) of the radiotherapy device 110. In some embodiments, the radiotherapy device 110 may include a PET-CT subsystem which includes the PET detector(s) and an X-ray detector. For example, the PET-CT subsystem may be mounted on the gantry 114 out of the treatment plane of the radiotherapy device 110.

In some embodiments, a PET detector may include one or more detector units. The detector units may be assembled in any suitable manner, for example, a ring, an arc, a rectangle, an array, or the like, or any combination thereof. For example, the PET detector units may form two PET detector arcs, which are symmetrically mounted on the gantry 114 and opposing each other as illustrated in FIG. 2. A detector unit may detect a radiation event (e.g., the pair of annihilation photons) emitted from the subject. In some embodiments, one or more coincidence events may be determined based on the interaction positions and the interaction times of a plurality of photons. If two photons are received and interact with two scintillators of two detector units within a certain time window (e.g., 1 nanosecond, 2 nanoseconds, 5 nanoseconds, 10 nanoseconds, 20 nanoseconds, etc.), the two photons may be deemed to come from the same annihilation (i.e., a pair of annihilation photons), and regarded as a coincidence event (or coincident event). The coincidence event may be assigned to a line of response (LOR) joining the two relevant detector units that have detected the coincidence event. The coincidence events that are assigned to LORs may be projected, and image data may be generated. In some embodiments, a detector unit may include one or more crystal elements (e.g., scintillators) and/or one or more photomultipliers (e.g., silicon photomultiplier (SiPM), photomultiplier tube (PMT)). In some embodiments, the PET detector(s) may be omitted from the radiotherapy device 110 and be part of a PET scanner. The PET scanner may be a component of the radiotherapy system 100 or a system other than the radiotherapy system 100.

The network 120 may include any suitable network that can facilitate the exchange of information and/or data for the radiotherapy system 100. In some embodiments, one or more components of the radiotherapy system 100 (e.g., the radiotherapy device 110, the terminal(s) 130, a processing device 140, and a storage device 150, etc.) may communicate information and/or data with one or more other components of the radiotherapy system 100 via the network 120. For example, the processing device 140 may obtain one or more images of an ROI of the subject from a scintillation camera 113 via the network 120. As another example, the processing device 140 may obtain a user instruction from the terminal(s) 130 via the network 120. The network 120 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the radiotherapy system 100 may be connected to the network 120 to exchange data and/or information.

The terminal(s) 130 may enable a user interaction between a user (e.g., a doctor, a physician) and one or more components of the radiotherapy system 100. For example, a terminal 130 may receive an instruction inputted by a user to direct a scintillation camera 113 to capture an image of the subject during a treatment session. As another example, a terminal 130 may display one or more images captured by a scintillation camera 113 to the user. The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data and/or information obtained from the radiotherapy device 110, the terminal(s) 130, and/or the storage device 150. For example, the processing device 140 may determine a position of the ROI based image(s) captured by the scintillation camera(s)

113. As another example, the processing device 140 may direct the radiotherapy device 110 to adjust a radiation beam based on the position of the ROI. In some embodiments, the processing device 140 may be a single server or a server group. The server group may be centralized or distributed. In some embodiments, the processing device 140 may be local or remote. For example, the processing device 140 may access information and/or data stored in the radiotherapy device 110, the terminal(s) 130, and/or the storage device 150 via the network 120. As another example, the processing device 140 may be directly connected to the radiotherapy device 110, the terminal(s) 130, and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2. In some embodiments, the processing device 140, or a portion of the processing device 140 may be integrated into the radiotherapy device 110.

The storage device 150 may store data, instructions, and/or any other information. In some embodiments, the storage device 150 may store data obtained from the radiotherapy device 110, the terminal(s) 130, and/or the processing device 140. For example, the storage device 150 may store a treatment plan and/or one or more images of the subject, or the like. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the radiotherapy system 100 (e.g., the processing device 140, the terminal(s) 130, etc.). One or more components of the radiotherapy system 100 may access the data or instructions stored in the storage device 150 via the network 120. In some embodiments, the storage device 150 may be directly connected to or communicate with one or more other components in the radiotherapy system 100 (e.g., the processing device 140, the terminal(s) 130, etc.). In some embodiments, the storage device 150 may be part of the processing device 140.

It should be noted that the above description of the radiotherapy system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the radiotherapy system 100 may include one or more additional components, such as an imaging component (e.g., a CT device). Additionally or alternatively, one or more components of the radiotherapy system 100 described above may be omitted. As another example, two or more components of the radiotherapy system 100 may be integrated into a single component.

Figure 1B:
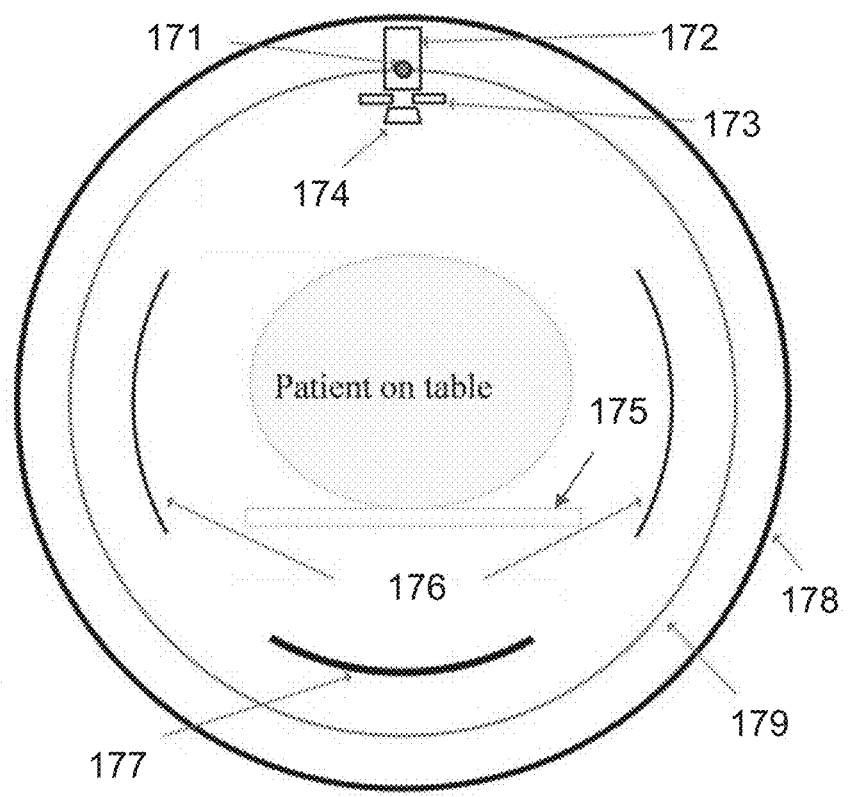
FIG. 1B is a schematic diagram illustrating an exemplary radiotherapy device according to some embodiments of the present disclosure.

FIG. 1B is a schematic diagram illustrating an exemplary radiotherapy device 170 according to some embodiments of the present disclosure. The exemplary radiotherapy device 170 may be an embodiment of the radiotherapy device 110 as described in connection with FIG. 1A. As shown in FIG. 1B, the radiotherapy device 170 may include a linear accelerator (Linac) module, a table 175, a PET detector arc pair 176, an X-ray detector 177, a gantry 178.

The Linac module may include a Linac source 171, a Linac accelerator 172, a primary collimator 173, and a multi-leaf collimator 174. The components of the Linac module may be configured to generate and emit a radiation beam of a certain shape toward a target of a subject to be treated. For example, the Linac source 171 may be configured to produce a plurality of charged particles, such as an ion, an electron, a proton, an atomic nucleus. The Linac accelerator 172 may be configured to accelerate the charged particles and generate a radiation beam. The radiation beam may pass through the primary collimator 173 and the multi-leaf collimator 174 forming a certain shape. The table 175 may be configured to support the subject during the radiation treatment. The PET detector arc pair 176 may include two PET detector arcs which are symmetrically opposed and have a similar function as the PET detector(s) described in FIG. 1A. The X-ray detector 177 may be used for subject setup and alignment of the target of the subject. In some embodiments, the X-ray detector 177 may be a megavoltage (MV) X-ray detector configured to detect MV X-rays. The gantry 178 may be configured to support one or more components of the radiotherapy device 170, such as the Linac module, the PET detector arc pair 176, and/or the X-ray detector 177.

In some embodiments, the gantry 178 may be rotatable along a slip-ring around a system isocenter of the radiotherapy device 170. One or more components, such as the Linac module, the X-ray detector 177, and the PET detector arc pair 176 may rotate with the gantry 178. For example, the Linac source 171 may rotate along a source trajectory 179 as shown in FIG. 1B. In some embodiments, the radiotherapy device 170 may further include one or more scintillation cameras (e.g., one or more scintillation cameras 113 as described in connection with FIG. 1) (not shown in FIG. 1B). For example, the scintillation camera(s) may be mounted on the gantry 178 and configured to capture one or more images of the subject during treatment for tracking the physiological motion of an ROI of the subject.

It should be noted that the above description of the radiotherapy device 170 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the radiotherapy device 170 may include one or more additional components and/or one or more components of the radiotherapy device 170 described above may be omitted. Additionally or alternatively, a component of the radiotherapy device 170 may be replaced by one or more other components that may implement the same or similar functions. For example, the Linac accelerator 172 may be replaced by any other types of accelerators. Merely by way of example, a particle accelerator, such as a cyclotron may be used as a source for ion therapy.

FIG. 2 is a schematic diagram illustrating exemplary hardware and/or software components of a computing device 200 according to some embodiments of the present disclosure. The computing device 200 may be used to implement any component of the radiotherapy system 100 as described herein. For example, the processing device 140 and/or the terminal(s) 130 may be implemented on the computing device 200, respectively, via its hardware, software program, firmware, or a combination thereof. Although only one such computing device is shown, for convenience, the computer functions relating to the radiotherapy system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the radiotherapy device 110, the terminal(s) 130, the storage device 150, and/or any other component of the radiotherapy system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data obtained from one or more components of the radiotherapy system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure. For example, the storage 220 may store a program for the processing device 140 to execute for motion tracking in a treatment session.

The I/O 230 may input and/or output signals, data, information, etc. In some embodiments, the I/O 230 may enable a user interaction with the processing device 140. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the processing device 140 and the radiotherapy device 110, the terminal(s) 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
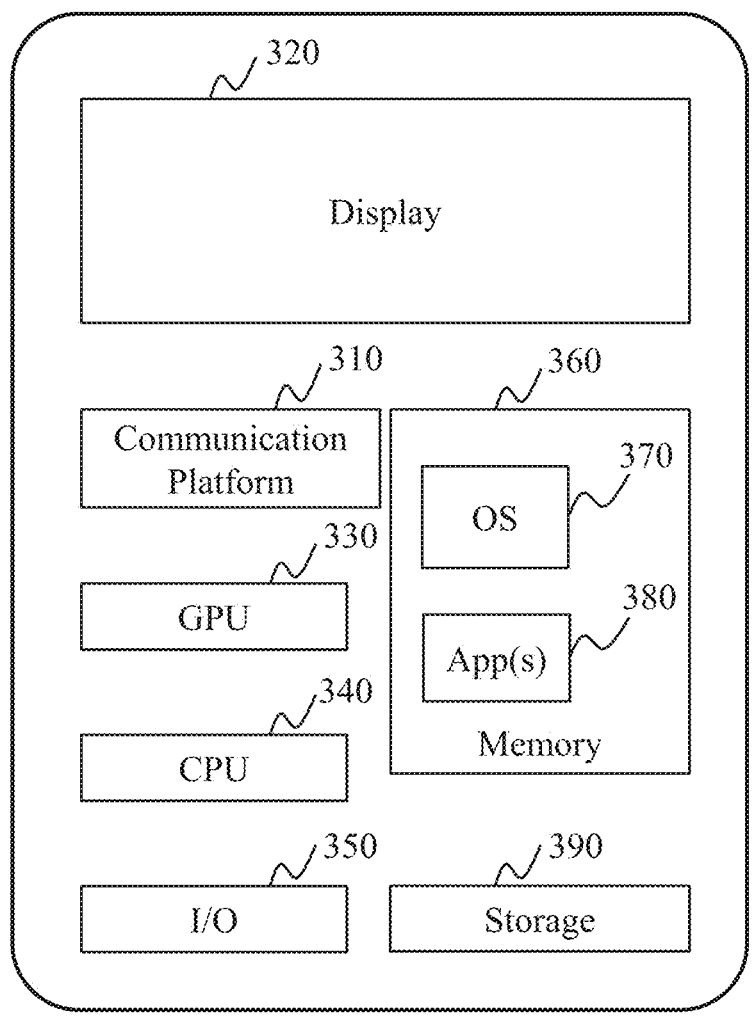
FIG. 3 is a schematic diagram illustrating exemplary hardware and/or software components of a mobile device according to some embodiments of the present disclosure.

FIG. 3 is a schematic diagram illustrating exemplary hardware and/or software components of an exemplary mobile device 300 according to some embodiments of the present disclosure. In some embodiments, a terminal 130 and/or a processing device 140 may be implemented on a mobile device 300, respectively. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to the radiotherapy system 100. User interactions with the information stream may be achieved via the I/O 350 and provided to the processing device 140 and/or other components of the radiotherapy system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
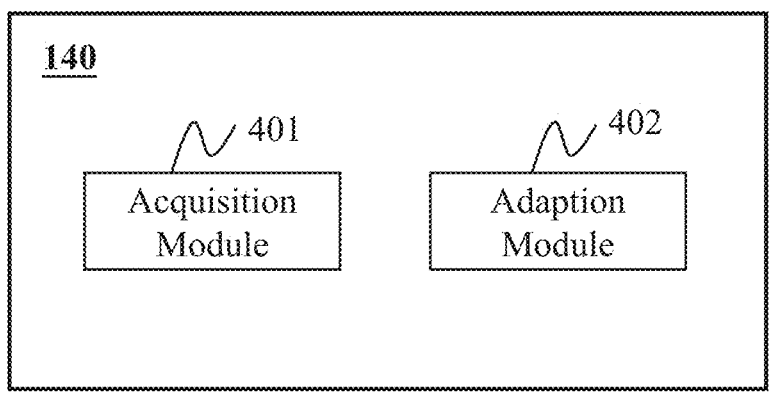
FIG. 4 is a schematic diagram illustrating an exemplary processing device according to some embodiments of the present disclosure.

FIG. 4 is a schematic diagram illustrating an exemplary processing device 140 according to some embodiments of the present disclosure. The processing device 140 may be configured to process information in a treatment session of a subject (e.g., a patient). In some embodiments, a radiotherapy device (e.g., the radiotherapy device 110) may be used to deliver the treatment session. The radiotherapy device may include a scintillation camera that is directed at an ROI of the subject. The subject may be injected with a radioactive tracer or implanted with a radioactive marker before treatment, and the ROI may undergo a physiological motion (e.g., a cardiac motion, a respiratory motion, etc.) during the treatment. The processing device 140 may include an acquisition module 401 and an adaption module 402.

The acquisition module 401 may be configured to acquire a target image of the ROI of the subject captured by the scintillation camera. The ROI of the subject may include a target and/or an OAR near the target. The scintillation camera may be configured to detect single photons from a plurality of pair of annihilation photons and acquire images indicative of a distribution of the radioactive tracer in the ROI. The target image may be indicative of a distribution of the radioactive tracer or the radioactive marker in the ROI at the time when the target image is captured by the scintillation camera. More descriptions regarding the acquisition of the target image may be found elsewhere in the present disclosure. See, e.g., operation 501 and relevant descriptions thereof.

The adaption module 402 may be configured to adapt a radiation beam to be delivered to the subject with respect to the physiological motion of the ROI by adjusting the radiation beam based on the target image. In some embodiments, the adaption module 402 may determine a target position of the ROI based on the target image. After the target position of the ROI is determined, the radiation beam may be adjusted based on the target position of the ROI. In some embodiments, the adaption module 402 may direct the radiotherapy device to gate a delivery of the radiation beam according to the target position of the ROI. Additionally or alternatively, the adaption module 402 may direct the radiotherapy device to aim the radiation beam at the target according to the target position of the ROI. More descriptions regarding the adaption of the radiation beam may be found elsewhere in the present disclosure. See, e.g., operation 502 and relevant descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 140 may include one or more additional modules and/or one or more modules described above may be omitted. Additionally or alternatively, two or more modules may be integrated into a single module and/or a module may be divided into two or more units. However, those variations and modifications also fall within the scope of the present disclosure.

FIG. 5 is a flowchart illustrating an exemplary process for adapting a radiation beam to be delivered to a subject with respect to a physiological motion of an ROI of the subject according to some embodiments of the present disclosure. In some embodiments, process 500 may be executed by the radiotherapy system 100. For example, the process 500 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and accordingly direct one or more components of the radiotherapy system 100 to perform the process 500.

As used herein, the subject may refer to a patient, a portion of a patient, or any organism that needs to be treated by a radiotherapy device (e.g., the radiotherapy device 110). An ROI of the subject may include a target and/or an OAR near the target. The ROI may undergo a physiological motion (e.g., a cardiac motion, a respiratory motion, etc.) during a treatment session. In order to facilitate an accurate delivery of the treatment session in the presence of the physiological motion of the ROI, the position of the ROI may need to be tracked in the treatment session.

In some embodiments, the radiotherapy device may include a scintillation camera (e.g., a scintillation camera 113 as described in connection with FIG. 1A) that is directed at the ROI. The position of the ROI may be tracked using the scintillation camera. For example, before the treatment session, the subject may be injected with a radioactive tracer, such as a PET tracer (e.g., FDG) or a SPECT tracer (e.g., HMPAO) or be implanted with a radioactive marker. Taking the radioactive tracer as an example, it may undergo positron emission decay and emit positrons. A positron may interact with an electron of the subject and produce a pair of annihilation photons (e.g., a 511 keV photon pair). The scintillation camera may be configured to detect single photons from a plurality of pair of annihilation photons and acquire images indicative of a distribution of the radioactive tracer in the ROI.

In some embodiments, the ROI may include a target to be treated and an OAR surrounding the target. Ideally, the target may have a specific uptake of the radioactive tracer with respect to the OAR such that the target may be distinguished from the OAR in an image captured by the scintillation camera. In some embodiments, two radioactive tracers (e.g., a PET tracer and a SPECT tracer) may be injected into the subject before the treatment session. The target may have a high uptake to one of the radioactive tracers and the surrounding OAR may have a high uptake to the other one of the radioactive tracers. For example, in prostate cancer treatment, a cancer-specific tracer (e.g., FDG, PSMA) that may accumulate in the prostate and another tracer that may accumulate within the rectum may be injected into the subject. In this way, both the rectum and the prostate may be tracked in the treatment session, which allows for rectal sparing when the rectum moves into the treatment field due to the rectal motion. In some alternative embodiments, a specific radioactive tracer may be injected and accumulate in the target, and a radioactive or X-ray attenuating fiducial may be placed in the OAR. The target and the OAR may be able to be identified in an image acquired by the scintillation camera. Alternatively, a specific radioactive tracer may be injected and accumulate in the target, and a radioopaque marker may be implanted in the OAR before the treatment session. During the treatment session, the scintillation camera and an X-ray imaging device may be used to acquire images of the ROI, wherein the target may be tracked according to image(s) acquired by the scintillation camera and the OAR may be tracked according to image(s) acquired by the X-ray imaging device. For example, a "barium meal" may be used in prostate cancer treatment, and the rectal content may be identified in an image acquired using the X-ray imaging device.

In some embodiments, the scintillation camera may be placed at a certain position according to the position of the ROI before the treatment session. For example, the scintillation camera may be placed close to the body surface of a portion of the subject which is adjacent to the ROI, so as to focus on the ROI and improve the imaging quality of the scintillation camera. Additionally or alternatively, the position of the scintillation camera may be determined according to the radiation beam to be delivered to the subject in the treatment session. In some embodiments, before the treatment session, the processing device 140 may determine the position of the scintillation camera based on a trajectory of the radiation beam to be delivered to the subject in the treatment session. For example, the scintillation camera may need to be placed at a position such that a radiation beam to be delivered according to the treatment plan does not traverse the scintillation camera in the treatment session, in order to prevent an interference with the delivery of the radiation beam. Merely by way of example, in a prostate radiotherapy treatment, a laterally-opposed proton beam may be emitted from a radiation source to the subject. The scintillation camera may be arranged at a position aiming at the prostate in a substantially anterior-posterior (A-P) direction and/or transperineally, thereby avoiding interfering with the delivery of the laterally-opposed proton beam.

In some embodiments, in a photon treatment, the scintillation camera may be arranged at a position to have a view for capturing a lateral motion of the ROI with respect to the radiation beam (e.g., a motion along a direction perpendicular to the radiation beam). Ideally, the scintillation camera may be arranged at a position to capture images from a beam's-eye-view (BEV) (i.e., a viewing point at the treatment radiation source looking out along the trajectory of the radiation beam) or a reverse BEV. However, the scintillation camera may block the radiation beam if it is mounted at a position to capture images from the BEV or be destroyed if it is mounted at a position to capture images from the reverse BEV. Thus, the scintillation camera may be mounted at a position to capture images from a view as close as possible to the BEV without (or substantially without) blocking the radiation beam. In a charged particle treatment, the scintillation camera may be mounted at a position, at which an angle between the trajectory of the radiation beam and a line connecting the scintillation camera and the isocenter of the radiotherapy device may be equal to (or substantially equal to) 90 degrees. In some embodiments, the scintillation camera and another scintillation camera (referred to as dual scintillation cameras) may be used in combination to capture images of the ROI from two views. The dual scintillation cameras may be mounted at their respective positions at which an angle between the trajectory of the radiation beam and a line connecting each scintillation camera and the isocenter of the radiotherapy device may be equal to (or substantially equal to) 45 degrees. In some embodiments, in a non-isocentric radiotherapy device, the dual scintillation cameras may be mounted at their respective positions at which an angle between the trajectory of the radiation beam and the camera view axis may be equal to (or substantially equal to) 45 degrees.

In some embodiments, the ROI may include a target and an OAR of the subject. A scintillation camera may be placed at a certain position such that the target and the OAR may be separated from each other in an image captured by the scintillation camera. Merely by way of example, the OAR and the target may share a tangent line, and the scintillation camera may be placed at a position to image along the tangent line.

In some embodiments, the subject may include a plurality of targets to be treated. The radiotherapy device may include a plurality of scintillation cameras. Each target may be tracked by one or more of the scintillation cameras. The position of a scintillation camera corresponding to a certain target may be determined based on the trajectory or trajectories of one or more radiation beam(s) to be delivered to the certain target.

During the treatment session delivered by the radiotherapy device, operations 501 and 502 may be performed to track the physiological motion of the ROI and adapt the radiation beam to be delivered to the subject with respect to the physiological motion of the ROI.

In 501, the processing device 140 (e.g., the acquisition module 401, the interface circuits of the processor 210) may acquire a target image of the ROI captured by the scintillation camera.

For example, the processing device 140 may transmit an instruction to the scintillation camera to capture an image of the ROI. In response to the instruction, the scintillation camera may capture an image of ROI as the target image and transmit the captured image to the processing device 140 directly or via a network (e.g., the network 120). As another example, the scintillation camera may be directed to capture images of the ROI during the treatment session continuously or intermittently (e.g., periodically). In some embodiments, after the scintillation camera captures an image, the scintillation camera may transmit the image to the processing device 140 as the target image for further analysis. In some embodiments, the acquisition of the target image by the scintillation camera, the transmission of the captured target image to the processing device 140, and the analysis of the target image may be performed substantially in real time so that the target image may provide information indicating a substantially real time status of the ROI.

The target image may be indicative of a distribution of the radioactive tracer or the radioactive marker in the ROI at the time when the target image is captured by the scintillation camera. For example, a dark-shading part of the target image or a part of the target image having pixels of low grey values may represent a sub-region of the ROI with a low tracer concentration, while a light-shading part of the target image or a part of the target image having pixels of high grey values may represent a sub-region of the ROI with a high tracer concentration, or vice versa.

In 502, the processing device 140 (e.g., the adaption module 402, the processing circuits of the processor 210)

may adapt the radiation beam to be delivered to the subject with respect to the physiological motion of the ROI by adjusting the radiation beam based on the target image.

In some embodiments, the processing device 140 may determine a target position of the ROI based on the target image. The target position of the ROI may refer to a predicted position of the ROI at the time when the target image is captured. For example, the target position of the ROI may be a current position where the ROI is located at the present moment (or substantially at the present moment). In some embodiments, the target position of the ROI may be determined based on a plurality of reference images corresponding to a plurality of motion phases of the ROI. A reference image corresponding to a certain motion phase of the ROI may be indicative of a distribution of the radioactive tracer or the radioactive maker in the ROI at the certain motion phase. Taking a lung as an instance, the target position of the lung may be determined based on a plurality of reference images of the lung, each of which corresponds to a certain respiratory phase and be indicative of a distribution of the radioactive tracer or the radioactive marker in the lung at the certain respiratory phase. In some embodiments, the processing device 140 may obtain the plurality of reference images of the ROI and determine the target position of the ROI based on a comparison of the target image with each of the reference images. For example, the processing device 140 may determine the target position by performing one or more operations in process 600 as described in connection with FIG. 6.

After the target position of the ROI is determined, the radiation beam may be adjusted based on the target position of the ROI. In some embodiments, the processing device 140 may direct the radiotherapy device to gate a delivery of the radiation beam according to the target position of the ROI. As used herein, "gating a delivery of a radiation beam" may refer to turning on and/or off the radiation beam during the treatment session according to the target position of the ROI. For example, the radiation beam may be turned on only when the ROI is at a certain position during a specific interval of a motion cycle of the ROI.

Taking a lung as an exemplary target to be treated, the lung may undergo a respiratory motion during the treatment session and need to be tracked to facilitate an accurate delivery of the radiation beam to the lung. A specific segment in a respiratory cycle (also referred to as a gate window in the respiratory cycle), during which the respiratory motion amplitude (or amount) of the lung may be minimal or below a threshold, may be determined. The gate window and the target position may be used to determine when the radiotherapy device (e.g., the LINAC of the radiotherapy device) needs to deliver the radiation beam toward the lung during the treatment session. For example, the target position may be used to determine a motion phase of the lung at the time when the target image is acquired (e.g., a current motion phase of the lung). If the determined motion phase is within the gate window, the radiation beam may be delivered to the lung according to the target position of the lung. If the determined motion phase is outside of the gate window, the delivery of the radiation beam toward the lung may be turned off. In some embodiments, the delivery of the radiation beam may be turned on or off by turning on or off the treatment radiation source of the radiotherapy device. In some embodiments, the treatment radiation source may remain on during a treatment session, while the delivery of the radiation beam toward the lung may be turned on or off, or the location/shape of the treatment beam aperture modified, or the radiation output rate modified, by adjusting one or more collimators or radiation power controls of the radiotherapy device.

Additionally or alternatively, the processing device 140 may direct the radiotherapy device to aim the radiation beam at the target according to the target position of the ROI. For example, the ROI may include a target to be treated, and the radiation beam may be caused to aim at the target (e.g., an isocenter of the target). As another example, the ROI may include an OAR adjacent to the target, the processing device 140 may estimate a position of the target according to the target position of the OAR and direct the radiotherapy device to aim the radiation beam at the target. In some embodiments, the processing device 140 may send an instruction to the radiotherapy device to control the movement and/or shape of one or more components of the radiotherapy device (e.g., a gantry, a collimator, a couch), so as to control the radiation beam to aim at the target. By gating the radiation beam and/or aiming the radiation beam at the target (tracking), the radiation beam may be delivered to the target more precisely during the treatment session, thereby reducing or avoiding an impact on a surrounding healthy organ or tissue by radiation treatment.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 500 may be accomplished with one or more additional operations not described and/or without one or more of the operations discussed above. For example, the process 500 may include one or more additional operations before 501 to inject a radioactive tracer into the subject or implant a radioactive maker into the subject, move the subject to a planned treatment position, and/or place the scintillation camera at a suitable position before the treatment session. In some embodiments, during the treatment session, operations 501 and 502 may be performed continuously or intermittently (e.g., periodically, or irregularly), so as to track the physiological motion of the ROI in real-time or intermittently, thereby improving the precision and accuracy of treatment delivery.

In some embodiments, in 501, a single target image may be obtained from a scintillation camera which includes a coded-aperture collimator and/or a multiple pinhole collimator. The single target image may include depth information of a gamma-ray source (e.g., an annihilation event that produces annihilation photons) in the ROI and be used to determine a target position of the ROI in 502. Alternatively, the radiotherapy device may include a plurality of scintillation cameras, e.g., dual scintillation cameras, directed at the ROI. In 501, the processing device 140 may acquire a target image from each of the scintillation cameras. In 502, the processing device 140 may determine a target position of the ROI based on the target images, which will be described in detail in connection with FIG. 6.

In some embodiments related to particle therapy treatment delivery, the one or more scintillation cameras may be employed for the additional purpose of monitoring the position of a Bragg peak of a particle beam, or correlates of the Bragg peak that serve to verify that the depth of dose deposition is consistent with the treatment plan. Merely by way of example, during the treatment session, the processing device 140 may determine the position of the Bragg peak based on the target image acquired by the scintillation camera. The processing device 140 may further evaluate the delivery of the treatment session based on the position of the Bragg peak, e.g., by comparing the position of the Bragg peak with its planned position as prescribed in the treatment plan.

FIG. 6 is a flowchart illustrating an exemplary process for adapting a radiation beam to be delivered to a subject based on a target image of the subject according to some embodiments of the present disclosure. In some embodiments, process 600 may be executed by the radiotherapy system 100. For example, the process 600 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and accordingly be directed to perform the process 600. In some embodiments, one or more operations of the process 600 may be performed to achieve at least part of operation 502 as described in connection with FIG. 5.

In 601, the processing device 140 (e.g., the acquisition module 401, the interface circuits of the processor 210) may obtain a plurality of reference images of the ROI corresponding to a plurality of motion phases of the ROI.

A reference image corresponding to a motion phase of the ROI may indicate a distribution of the radioactive tracer or the radioactive marker in the ROI at the motion phase. Merely by way of example, the ROI may include the heart of the subject, such as is particularly relevant for deep inhalation breathhold radiation therapy of the breast ipsilateral to the heart. A cardiac cycle may include systole (during which the left and right ventricles contract and eject blood into the aorta and pulmonary artery, respectively) and diastole (during which the ventricles are relaxed). The cardiac cycle may be divided into a plurality of cardiac phases, such as 5 or 10 cardiac phases depending on, for example, the heart rate and/or movement amplitude of the heart. A reference image of the heart may correspond to one of the cardiac phases and indicate the distribution of the radioactive tracer or the radioactive maker in the corresponding cardiac phase. As another example, the ROI may include a lung of the subject. A respiratory cycle may include an inspiratory phase (during which the chest of the subject expands and air flows into the lungs) and an expiratory phase (during which the chest shrinks and the air is pushed out of the lungs). The respiratory cycle may be gated into a plurality of respiratory phases, such as 4 respiratory phases including a mid-inspiratory phase, an end-inspiratory phase, a mid-expiratory phase, and an end-expiratory phase according to, for example, time or the amplitude of the respiratory motion. A reference image of the lung may correspond to one of the respiratory phases and indicate the distribution of the radioactive tracer or the radioactive maker in the corresponding respiratory phase.

In some embodiments, the reference images may include one or more actual images captured by the scintillation camera that acquires the target image or another scintillation camera. Additionally or alternatively, the reference images may include one or more simulated images generated by the processing device 140 (or another computing device). More descriptions regarding the generation of the reference images may be found elsewhere in the present disclosure. See, e.g., 602 and relevant descriptions thereof.

In 602, the processing device 140 (e.g., the acquisition module 401, the interface circuits of the processor 210) may obtain an image sequence relating to the ROI.

The image sequence may include a plurality of images corresponding to the motion phases of the ROI. In some embodiments, the image sequence may be a PET image sequence or a SEPCT image sequence. As described in connection with FIG. 5, the subject may be injected with a PET tracer or a SPECT tracer before the treatment session. A PET image sequence may be acquired in 602 if the subject is injected with a PET tracer, and a SPECT image sequence may be acquired if the subject is injected with a SPECT tracer. Alternatively, the image sequence may be a CT image sequence including a plurality of CT images of the subject.

Each image in the image sequence may represent one of the motion phases of the ROI and correspond to a reference image of the same motion phase. Merely by way of example, as described in connection with 601, the reference images may include 10 reference images representing a distribution of the radioactive tracer or the radioactive maker in the heart in 10 cardiac phases. The image sequence may include 10 images corresponding to the 10 cardiac phases. An image and a reference image of the same cardiac phase may be deemed as corresponding to each other. In some embodiments, because that the target image captured by the scintillation camera may provide less information (e.g., information for determining the target position of the ROI) than an image in the imaging sequence (e.g., a PET image, a CT image), the target position of the ROI may be determined based on the image sequence and the reference images. In this way, the target position of the ROI may be estimated more accurately and precisely. Even in cases that the ROI is not clear enough in the target image, an accurate position estimation of the ROI may be achieved based on the corresponding relationship between the images in the image sequence and the reference images.

In some embodiments, the image sequence may be generated by performing a scan on the subject. For example, after the subject is injected with a radioactive tracer and before the treatment session as described in FIG. 5, a scan may be performed on the subject using a scanner. Merely by way of example, before the treatment session starts, a PET scan may be performed on the subject using a PET scanner. Alternatively, before the treatment session starts, a CT scan may be performed on the subject using a CT scanner. The scanner (e.g., the PET scanner, the CT scanner) may be an independent scanner or be part of the radiotherapy device for delivering the treatment session. The images in the image sequence may be reconstructed based on image data acquired in the scan of the subject. Merely by way of example, during a PET scan, a motion signal representing the physiological motion of the ROI (e.g., an electrocardiogram (ECG) signal representing the cardiac motion) may be acquired. A motion cycle of the ROI may be divided into a plurality of motion phases according to the motion signal, and the PET data acquired in the PET scan may be gated into a plurality of PET data sets corresponding to the respective motion phases. Then, the PET images may be reconstructed based on the gated PET data sets. In some embodiments, the image sequence may be previously generated and stored in a storage device (e.g., the storage device 150, the storage 220, the storage 390, or an external source). The processing device 140 may retrieve the image sequence from the storage device.

In some embodiments, the reference images may be actual images captured one or more scintillation cameras before, during, or after the acquisition of the image sequence (i.e., the pretreatment scan of the subject as aforementioned). The scintillation camera(s) may include or be without the scintillation camera that captures the target image as described in connection with FIG. 5. Merely by way of example, the reference images and the image sequence may both be acquired during a PET scan of the subject. During the PET scan, a scintillation camera of the radiotherapy device may be aimed at the ROI (e.g., placed at or close to a portion of the body surface of the subject near the ROI) to capture the reference images of the ROI. Optionally, the scintillation camera that captures the reference images may be placed at the same position relative to the ROI as the scintillation camera that captures the target image. The simultaneous PET scan and scintillation imaging may acquire the PET images and the reference images, and also establish a corresponding relationship between the PET images and the reference images. Optionally, the corresponding relationship between the positions (or a moving trajectory) of the ROI and the reference images (or different motion phases of the ROI) may also be established based on the simultaneous PET scan and scintillation imaging.

Alternatively, the image sequence may be a PET image sequence or a SPECT image sequence, and the reference images of the ROI may be generated based on the image sequences according to a simulation algorithm (e.g., a Monte Carlo algorithm). Taking a PET image sequence as an instance, a reference image corresponding to a certain motion phase may be generated by simulation based on a PET image corresponding to the certain motion phase. In some embodiments, a PET scan of the subject may be performed by a PET scanner without one or more scintillation cameras present. This may improve the quality of the PET images, since the scintillation camera(s) may be out of the field-of-view (FOV) of the PET detector(s). In some embodiments, the PET scan of the subject may be performed by a PET scanner with one or more scintillation cameras in the FOV of the PET detectors. The PET images may be reconstructed based on PET data according to a PET image reconstruction model that incorporates the scintillation camera(s), thereby mitigating the effect of the scintillation camera(s) and improving the quality of the PET images.

In 603, the processing device 140 (e.g., the adaption module 402, the processing circuits of the processor 210) may select a reference image that matches the target image among the plurality of reference images by comparing the target image with the reference images.

In some embodiments, a comparison result between the target image and a reference image may include any metrics for measuring the extent of similarity (or also referred to as a similarity degree) between the two images. Merely by way of example, the similarity degree between the target image and a reference image may be determined based on an image similarity algorithm, including a peak signal to noise ratio (PSNR) algorithm, a structural similarity (SSIM) algorithm, a perceptual hash algorithm, a cosine similarity algorithm, a histogram-based algorithm, an Euclidean distance-based algorithm, or the like, or any combination thereof.

The reference image that best matches the target image among the reference images may be identified according to the similarity degree between the target image and each of at least some of the reference images. Merely by way of example, the reference image that has the highest similarity degree with the target image among the reference images may be selected as the one that matches the target image. As another example, the reference image that has a similarity degree with the target image greater than a threshold may be selected as the one that matches the target image. The target image and the selected reference image matching the target image may be regarded as being corresponding to the same or substantially the same motion phase of the ROI. For the convenience of descriptions, the motion phase of the target image and the selected reference image may be referred to as a target motion phase.

In some embodiments, the reference images may be acquired or simulated for a plurality of observation angles (e.g., a plurality of gantry angles). For example, during the treatment session, the scintillation camera may be moved to different positions, e.g., with the rotation of the gantry, to capture image(s) from different perspectives. The target image captured by the scintillation camera at a certain gantry angle may be compared with reference images acquired or simulated for the certain gantry angle.

In 604, the processing device 140 (e.g., the adaption module 402, the processing circuits of the processor 210) may determine the target position of the ROI based on the image corresponding to the selected reference image in the image sequence. For brevity, the image corresponding to the selected reference image may be referred to as a selected image.

The selected image may correspond to the same motion phase of the ROI as the selected reference image. In other words, the target image and the selected image may both correspond to the target motion phase of the ROI. The target position at which the ROI is located when the target image is acquired may be determined based on the selected image. For example, the processing device 140 may determine the position of the ROI at the target motion phase by analyzing the selected image, and designate the determined position as the target position of the ROI.

In some embodiments, as described in connection with FIG. 5, a plurality of scintillation cameras may be configured to capture a plurality of target images of the ROI during the treatment session. In 602, each of the target images may be compared with the reference images to select a reference image that matches the target image. Merely by way of example, dual scintillation cameras may be utilized to capture a first target image of the ROI from a first view and a second target image of the ROI from a second view, respectively. The reference images obtained in 601 may include a first set of reference images corresponding to the plurality of motion phases of the ROI and a second set of reference images corresponding to the plurality of motion phases of the ROI. The first set of reference images may include actual images or simulated images of the ROI from a same view as or a similar view to the first view. The second set of reference images may include actual images or simulated images of the ROI from a same view as or a similar view to the second view. The first target image may be compared with the first set of the reference images to determine a first selected reference image that matches the first target image. The second target image may be compared with second set of reference images to determine a second selected reference image that matches the second target image. If the first selected reference image and the second selected reference image both correspond to a certain motion phase of the ROI, the first target image and the second target image may be deemed as corresponding to the certain motion phase. The target position of the ROI may be determined based on the image that corresponds to the certain motion phase in the image sequence.

In 605, the processing device 140 (e.g., the adaption module 402, the processing circuits of the processor 210) may adjust the radiation beam based on the target position of the ROI.

In some embodiments, the processing device 140 may direct the radiotherapy device to gate a delivery of the radiation beam according to the target position of the ROI. Additionally or alternatively, the processing device 140 may direct the radiotherapy device to aim the radiation beam at a target according to the target position of the ROI. More descriptions regarding the adjusting of the radiation beam may be found elsewhere in the present disclosure. See, e.g., operation 502 in FIG. 5 and relevant descriptions thereof.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 600 may be accomplished with one or more additional operations not described and/or without one or more of the operations discussed above. For example, operations 601 and 602 may be integrated into a single operation.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for emission guided radiation therapy (EGRT), comprising:
a scintillation camera directed at a region of interest (ROI) of a subject who is receiving a radiation treatment, wherein the subject is injected with a radioactive tracer or implanted with a radioactive marker before the radiation treatment, the ROI undergoes a physiological motion during the radiation treatment, and the scintillation camera is configured to detect single photons from annihilation photon pairs produced by interactions between the radioactive tracer or the radioactive marker and the subject; and
a processing device configured to adaptively adjust the delivery of the radiation treatment with respect to the physiological motion of the ROI by:
obtaining a plurality of reference images of the ROI corresponding to a plurality of motion phases of the ROI, each of the reference images being indicative of a distribution of the radioactive tracer or the radioactive maker in the ROI at a corresponding motion phase; and
adaptively adjusting, based on the single photons detected by the scintillation camera and the plurality of reference images, the delivery of a radiation beam with respect to the physiological motion of the ROI.

2. The system of claim 1, wherein
the scintillation camera is further configured to generate a target image of the ROI indicative of a distribution of the radioactive tracer or the radioactive maker in the ROI based on the detected single photons, and
to adaptively adjust the delivery of the radiation treatment with respect to the physiological motion of the ROI, the processing device is further configured to:
acquire the target image from the scintillation camera; and
adaptively adjust the delivery of the radiation beam with respect to the physiological motion of the ROI based on the target image and the plurality of reference images.

3. The system of claim 2, wherein to adaptively adjust the delivery of the radiation beam with respect to the physiological motion of the ROI based on the target image and the plurality of reference images, the processing device is further configured to:
determine, based on the target image and the plurality of reference images, a target position of the ROI during the acquisition of the target image; and
adjust, based on the target position of the ROI, the radiation beam.

4. The system of claim 3, wherein the ROI includes at least one of a target or an organ at risk (OAR) near the target, and to adjust, based on the target position of the ROI, the radiation beam, the processing device is further configured to:
direct the radiotherapy device to gate a delivery of the radiation beam or aim the radiation beam at the target according to the target position of the ROI.

5. The system of claim 3, wherein to determine a target position of the ROI, the processing device is further configured to:
obtain an image sequence relating to the ROI, each image in the image sequence representing one motion phase of the plurality of motion phases and corresponding to a reference image of the same motion phase;
select, among the plurality of reference images, a reference image that matches the target image; and
determine, based on the image in the image sequence corresponding to the selected reference image, the target position of the ROI.

6. The system of claim 5, wherein to obtain a plurality of reference images of the ROI, the processing device is further configured to:
generate, based on the image sequence, the plurality of reference images of the ROI according to a simulation algorithm; or
obtain the plurality of reference images that are captured by the scintillation camera during a scan of the subject, the image sequence being reconstructed based on scan data collected by the scan.

7. The system of claim 6, wherein the scan of the subject is at least one of a positron emission tomography (PET) scan, a single-photon emission computed tomography (SPECT), or a computed tomography (CT) scan.

8. The system of claim 1, wherein the processing device is further configured to:
determine, based on a trajectory of the radiation beam, a position of the scintillation camera, wherein the scintillation camera is placed at the determined position during the radiation treatment.

9. The system of claim 2, wherein the radiotherapy device is a particle radiotherapy device that delivers a particle beam to the subject during the radiation treatment, and the processing device is further configured to:
determine, based on the target image, a position of a Bragg peak of the particle beam; and
evaluate, based on the position of the Bragg peak, the delivery of the radiation treatment.

10. The system of claim 1, wherein the scintillation camera is placed close to the body surface of the subject in the radiation treatment.

11. The system of claim 1, wherein the scintillation camera includes at least one of a $LaBr_3$:Ce scintillation camera, a $LaBr_3$(Ce+Sr) scintillation camera, or a cryogenic scintillation camera.

12. The system of claim 1, wherein the scintillation camera includes:
one or more low-afterglow scintillation crystals; and
a collimator operably coupled to the one or more low-afterglow scintillation crystals.

13. A method for emission guided radiation therapy (EGRT), the method comprising:
detecting, by a scintillation camera directed at a region of interest (ROI) of a subject who is receiving a radiation treatment, single photons from annihilation photon pairs produced by interactions between the subject and a radioactive tracer injected into the subject or a radioactive marker implanted into the subject, the ROI undergoing a physiological motion during the radiation treatment; and
adaptively adjusting, by a processing device, the delivery of the radiation treatment with respect to the physiological motion of the ROI by:
obtaining a plurality of reference images of the ROI corresponding to a plurality of motion phases of the ROI, each of the reference images being indicative of a distribution of the radioactive tracer or the radioactive maker in the ROI at a corresponding motion phase; and
adaptively adjusting, based on the single photons detected by the scintillation camera and the plurality of reference images, the delivery of a radiation beam with respect to the physiological motion of the ROI.

14. The method of claim 13, further comprising:
generating, by the scintillation camera, a target image of the ROI indicative of a distribution of the radioactive tracer or the radioactive maker in the ROI based on the detected single photons, and wherein
the adaptively adjusting, based on the single photons detected by the scintillation camera and the plurality of reference images, the delivery of a radiation beam with respect to the physiological motion of the ROI comprises:
acquiring the target image from the scintillation camera; and
adaptively adjusting the delivery of the radiation beam with respect to the physiological motion of the ROI based on the target image and the plurality of reference images.

15. The method of claim 14, wherein the adaptively adjusting the delivery of the radiation beam with respect to the physiological motion of the ROI based on the target image and the plurality of reference images comprises:
determining, based on the target image and the plurality of reference images, a target position of the ROI during the acquisition of the target image; and
adjusting, based on the target position of the ROI, the radiation beam.

16. The method of claim 15, wherein the ROI includes at least one of a target or an organ at risk (OAR) near the target, and the adjusting, based on the target position of the ROI, the radiation beam comprises:
directing the radiotherapy device to gate a delivery of the radiation beam or aim the radiation beam at the target according to the target position of the ROI.

17. The system of claim 15, wherein the determining a target position of the ROI comprises:
obtaining an image sequence relating to the ROI, each image in the image sequence representing one motion phase of the plurality of motion phases and corresponding to a reference image of the same motion phase;
selecting, among the plurality of reference images, a reference image that matches the target image; and
determining, based on the image corresponding to the selected reference image in the image sequence, the target position of the ROI.

18. The system of claim 17, wherein the obtaining a plurality of reference images of the ROI comprises:
generating, based on the image sequence, the plurality of reference images of the ROI according to a simulation algorithm; or
obtaining, by the scintillation camera, the plurality of reference images during a scan of the subject, the image sequence being reconstructed based on scan data collected by the scan.

19. The system of claim 18, wherein the scan of the subject is at least one of a positron emission tomography (PET) scan, a single-photon emission computed tomography (SPECT), or a computed tomography (CT) scan.

20. A non-transitory computer readable medium, comprising a set of instructions for emission guided radiation therapy (EGRT), wherein when executed by a radiotherapy system, the set of instructions direct the radiotherapy system to effectuate a method, the radiotherapy system comprising a scintillation camera and a processing device, the method comprising:
detecting, by the scintillation camera directed at a region of interest (ROI) of a subject who is receiving a radiation treatment, single photons from annihilation photon pairs produced by interactions between the subject and a radioactive tracer injected into the subject or a radioactive marker implanted into the subject, the ROI undergoing a physiological motion during the radiation treatment;
adaptively adjusting, by the processing device, the delivery of the radiation treatment with respect to the physiological motion of the ROI by:
obtaining a plurality of reference images of the ROI corresponding to a plurality of motion phases of the ROI, each of the reference images being indicative of a distribution of the radioactive tracer or the radioactive maker in the ROI at a corresponding motion phase; and
adaptively adjusting, based on the single photons detected by the scintillation camera and the plurality of reference images, the delivery of a radiation beam with respect to the physiological motion of the ROI.

* * * * *